United States Patent
Gibson et al.

(10) Patent No.: US 11,986,608 B2
(45) Date of Patent: May 21, 2024

(54) STEERABLE CATHETER HANDLE DESIGN

(71) Applicant: Boston Scientific Scimed Inc, Maple Grove, MN (US)

(72) Inventors: Charles A Gibson, Malden, MA (US); Charles E. Brown, Haverhill, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 690 days.

(21) Appl. No.: 16/998,181

(22) Filed: Aug. 20, 2020

(65) Prior Publication Data

US 2021/0052853 A1    Feb. 25, 2021

Related U.S. Application Data

(60) Provisional application No. 62/889,311, filed on Aug. 20, 2019.

(51) Int. Cl.
*A61M 25/01* (2006.01)

(52) U.S. Cl.
CPC .... *A61M 25/0147* (2013.01); *A61M 25/0136* (2013.01)

(58) Field of Classification Search
CPC ...................... A61M 25/0136; A61M 25/0147
See application file for complete search history.

(56) References Cited

U.S. PATENT DOCUMENTS

| | | | |
|---|---|---|---|
| 5,571,085 A | 11/1996 | Accisano | |
| 5,741,320 A * | 4/1998 | Thornton | A61M 25/0147 604/95.01 |
| 6,210,407 B1 | 4/2001 | Webster | |
| 2014/0194813 A1 | 7/2014 | Grunewald | |
| 2015/0231366 A1 * | 8/2015 | Davies | A61M 25/0136 604/95.04 |
| 2018/0272108 A1 | 9/2018 | Padilla et al. | |

FOREIGN PATENT DOCUMENTS

| | | | |
|---|---|---|---|
| EP | 1005839 A1 | 6/2000 | |
| EP | 0985423 B1 | 4/2006 | |
| EP | 2752218 A1 | 7/2014 | |
| EP | 3381394 A1 | 10/2018 | |
| JP | 2012-176163 A | 9/2012 | |
| WO | 96/37252 A1 | 11/1996 | |
| WO | WO-9637252 A1 * | 11/1996 | ........ A61M 25/0136 |

OTHER PUBLICATIONS

International Search Report and Written Opinion received for PCT Patent Application No. PCT/US2020/047114, dated Dec. 9, 2020, 12 pages.

* cited by examiner

*Primary Examiner* — Phillip A Gray
*Assistant Examiner* — Nidah Hussain
(74) *Attorney, Agent, or Firm* — Nelson Mullins Riley & Scarborough LLP

(57) ABSTRACT

Various aspects of the present disclosure are directed toward apparatuses, systems, and methods that include a housing; a catheter shaft and an actuator coupled to the catheter shaft and configured to move longitudinally relative to the housing and longitudinally move the catheter shaft in response to force imparted by a user. The apparatuses, systems, and methods may also include a piston assembly arranged within the housing and configured to receive the actuator and allow longitudinal movement of the actuator relative to the housing.

12 Claims, 7 Drawing Sheets

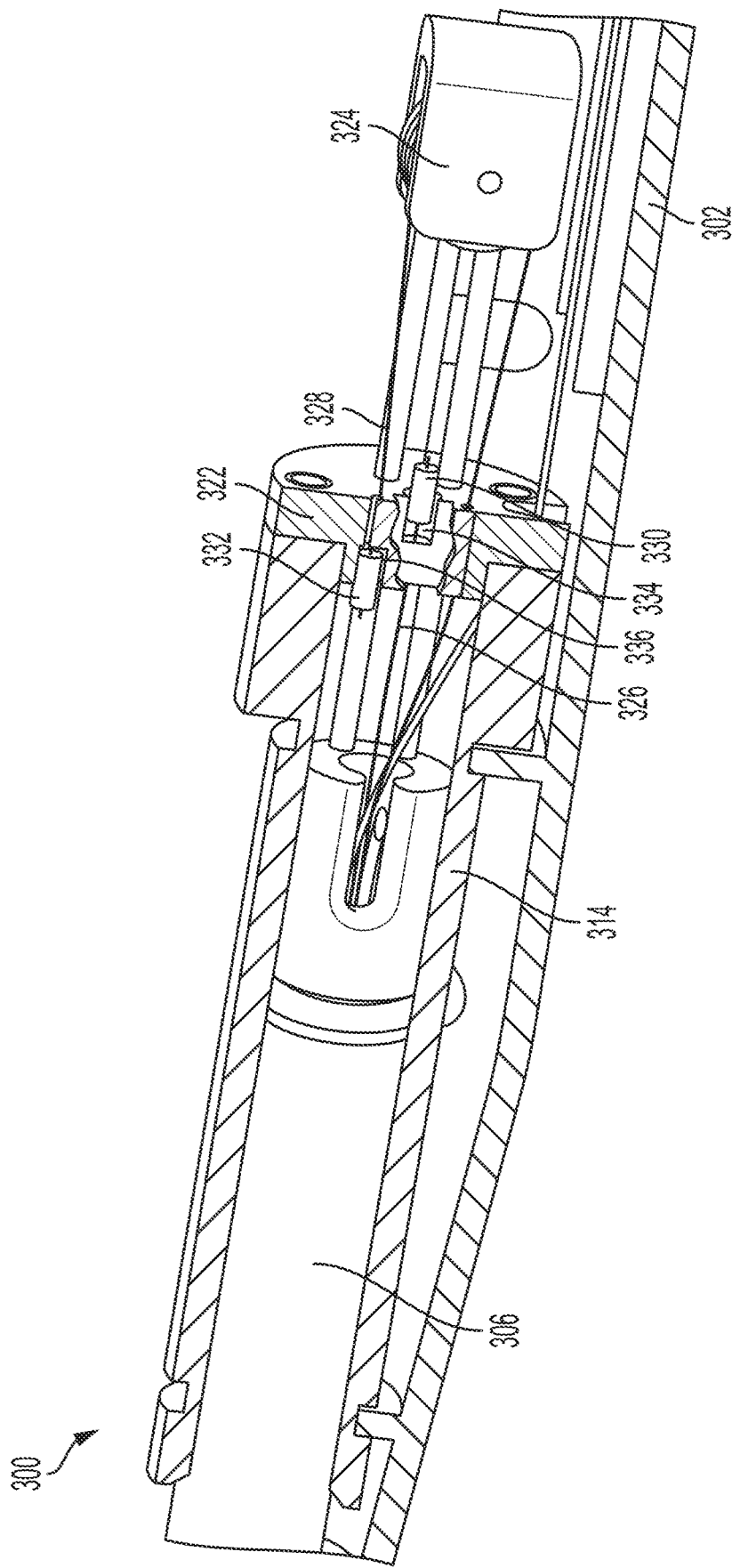

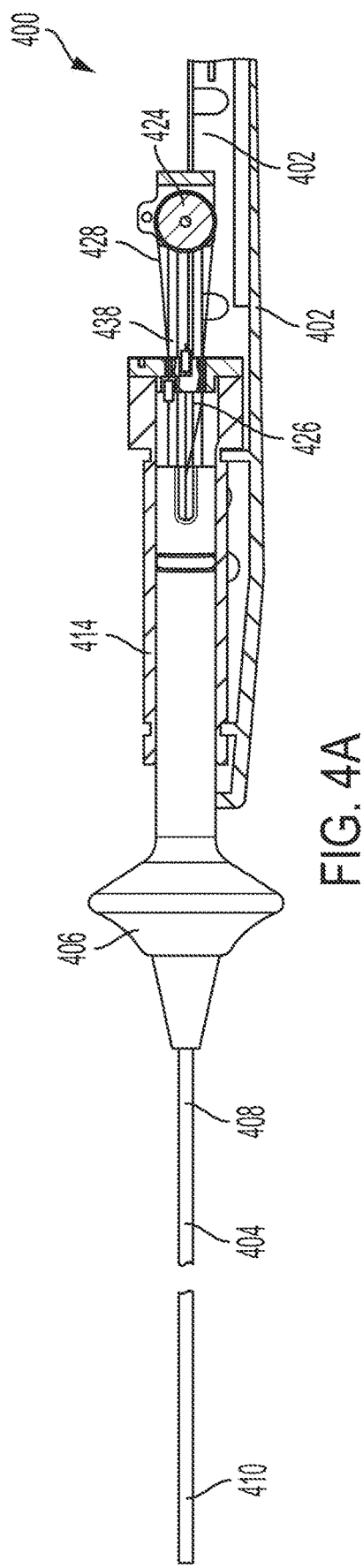
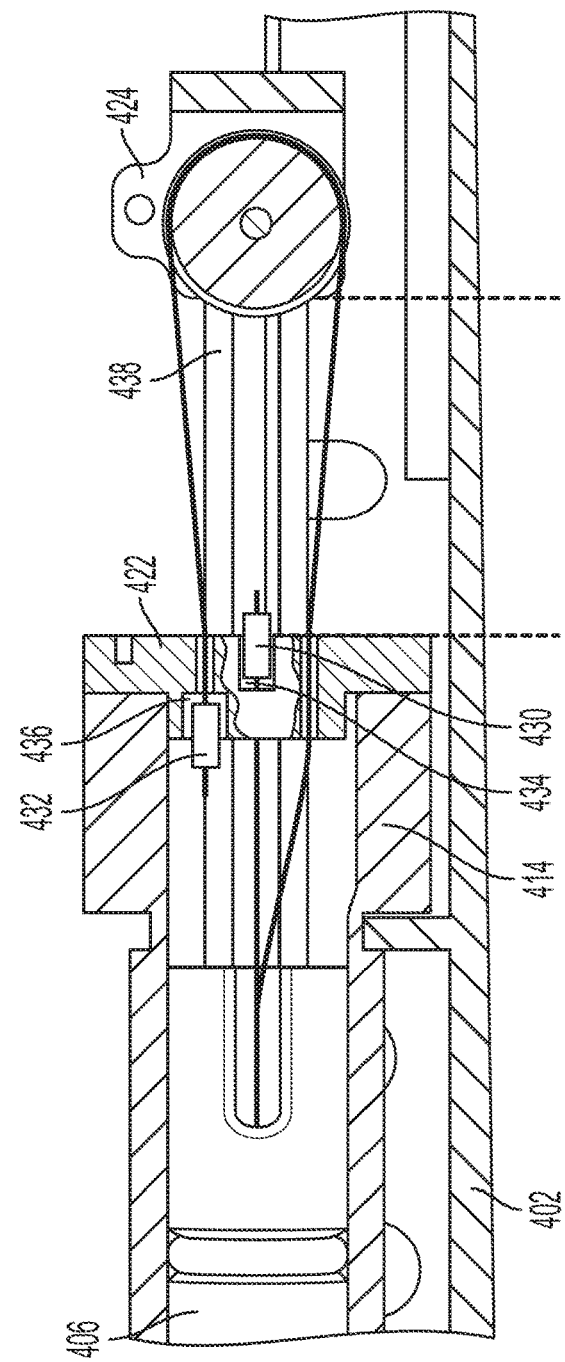
FIG. 4A
FIG. 4B

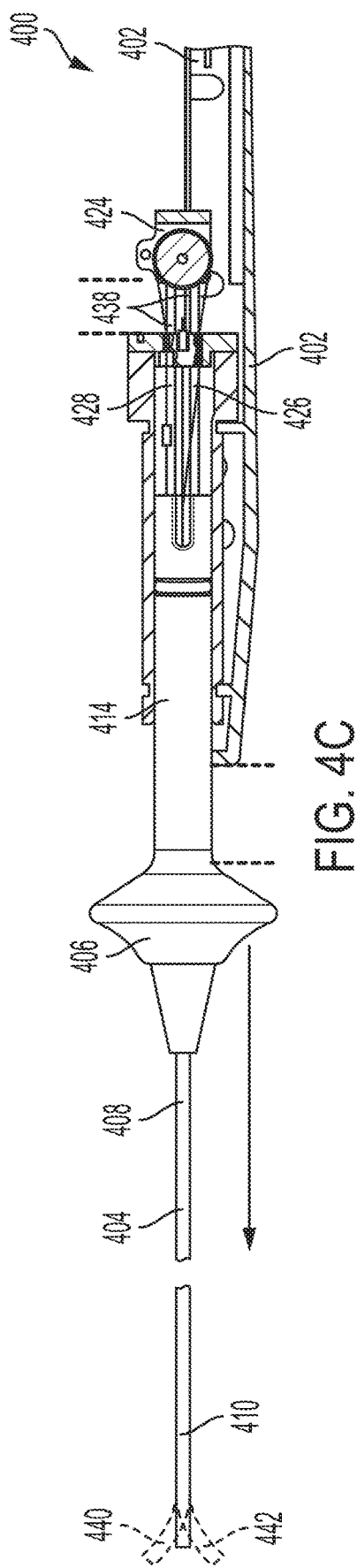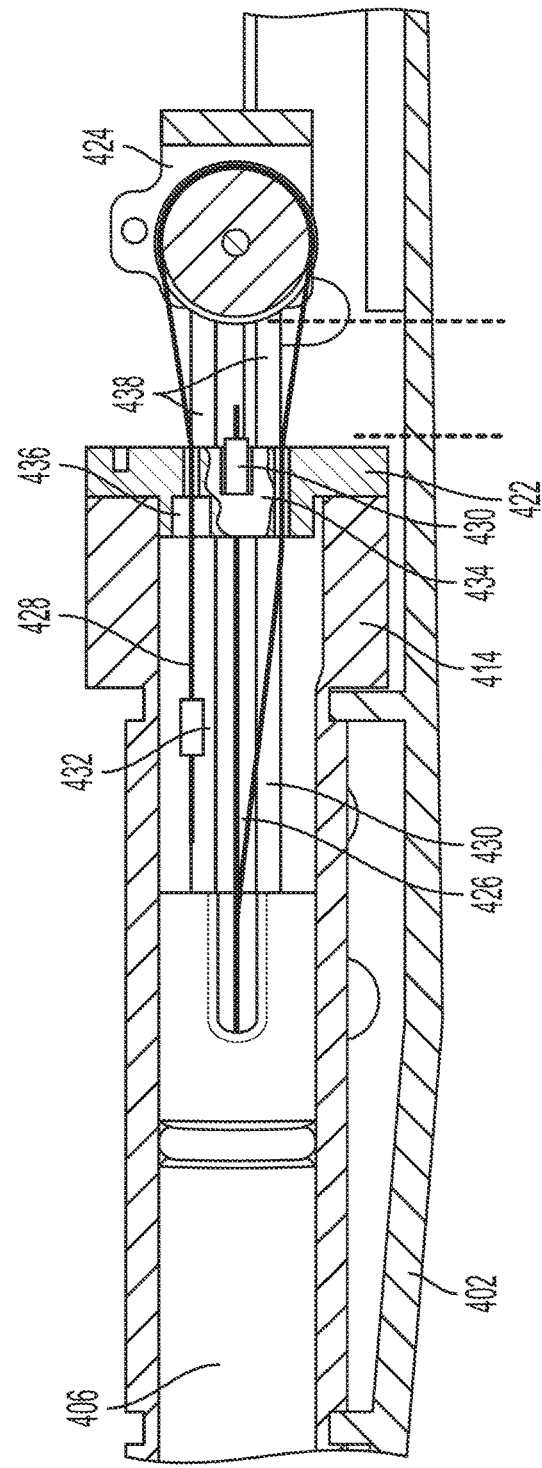
FIG. 4C
FIG. 4D

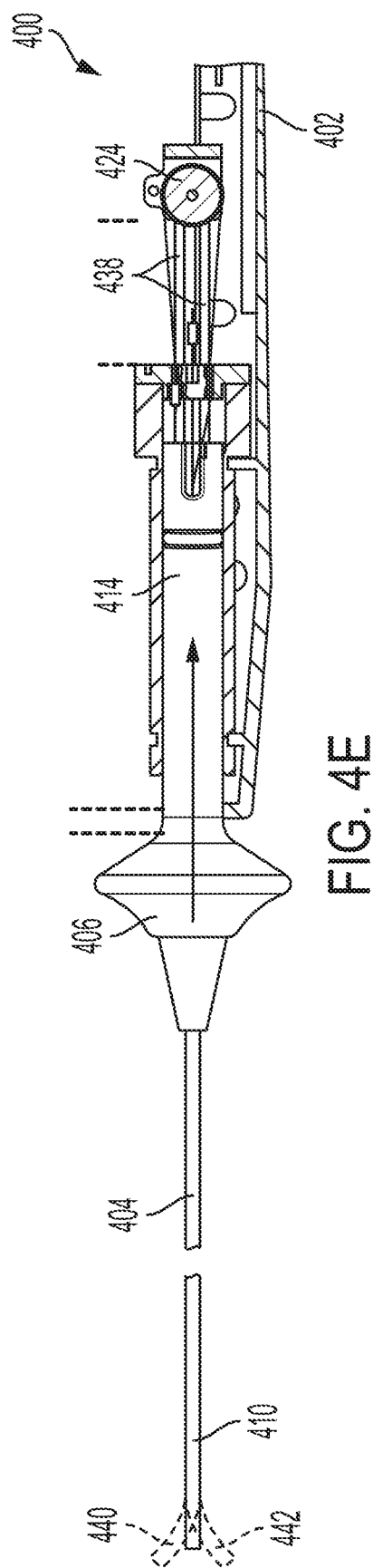
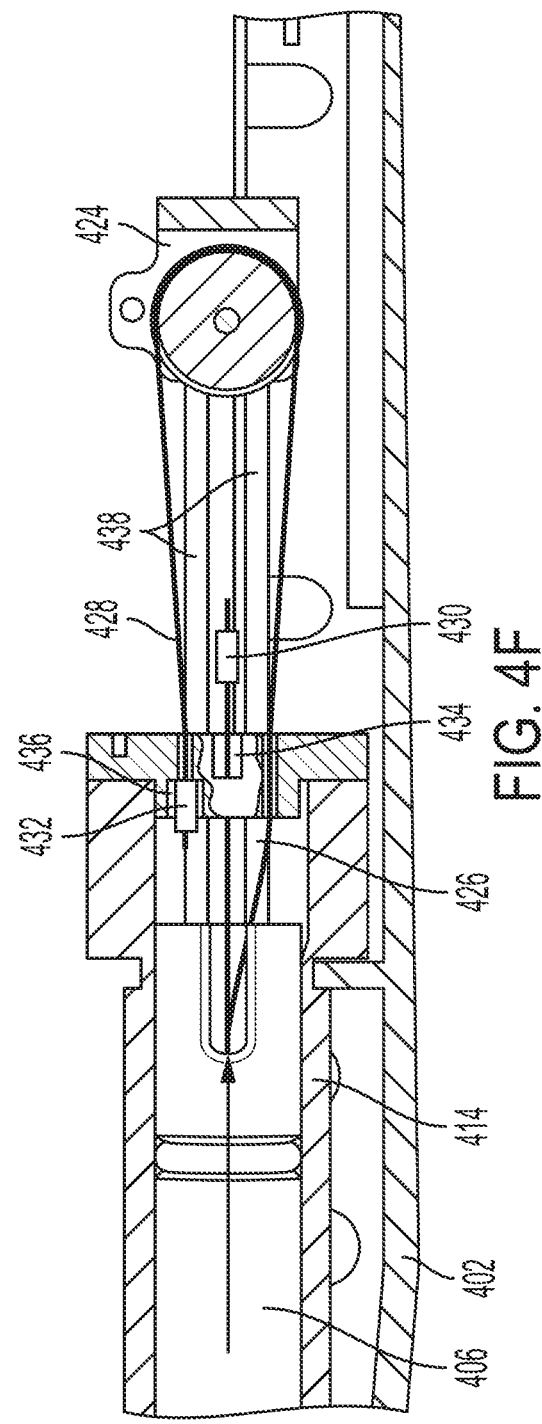

STEERABLE CATHETER HANDLE DESIGN

CROSS REFERENCE TO RELATED APPLICATION

This application claims priority to Provisional Application No. 62/889,311, filed Aug. 20, 2019, which is herein incorporated by reference in its entirety.

TECHNICAL FIELD

The present invention relates to catheter handles and methods of using the catheter handles. More specifically, the invention relates to catheter handles and methods of use having a deflectable distal end portion.

BACKGROUND

Steering mechanisms are used to steer or direct a medical instrument, for example a catheter coupled to a catheter handle, at a desired position or location in a body of a patient. The catheters may be used in medical procedures involving the controlled delivery of therapeutic energy to patient tissue. Steering or deflecting of an end portion of the catheter may enable delivery of energy to the target location of the patient tissue without substantial movement of the entire catheter handle.

SUMMARY

In Example 1, an apparatus includes a housing; a catheter shaft having a proximal portion, a distal portion, and an intermediate portion extending between the proximal portion and the distal portion; an actuator coupled to the catheter shaft and configured to move longitudinally relative to the housing and longitudinally move the catheter shaft in response to force imparted by a user; a piston assembly arranged within the housing and configured to receive the actuator and allow longitudinal movement of the actuator relative to the housing; and one or more lines including a distal end attached to the distal portion of the catheter shaft and a proximal portion configured to engage an end cap of the piston assembly in response to the longitudinal movement of the actuator to effect curvature of the distal portion of the catheter shaft.

In Example 2, further to the apparatus of Example 1, the apparatus also includes a pulley assembly arranged within the housing and configured to translate with the actuator in response to force imparted by the user on the actuator.

In Example 3, further to the apparatus of any one of Examples 1-2, the one or more lines is arranged about the pulley assembly.

In Example 4, further to the apparatus of any one of Examples 1-3, the one or more lines include a first line and a second line, and further comprising a first anchor attached to the proximal end of the first line, and a second anchor attached to the proximal end of the second line.

In Example 5, further to the apparatus of Example 4, the first anchor is configured to engage the end cap of the piston assembly in response to the movement of the actuator.

In Example 6, further to the apparatus of Example 5, the end cap of the piston assembly includes a first pocket and a second pocket, and the first anchor is configured to engage the first pocket of the piston assembly, and the second anchor is configured to engage the second pocket of the piston assembly in response to movement of the actuator.

In Example 7, further to the apparatus of Example 6, the actuator is configured to create tension on the first line to engage the first anchor with the first pocket in response to movement of the actuator in a distal direction relative to the housing.

In Example 8, further to the apparatus of Example 7, the actuator is configured to apply the tension on the first line to curve the distal portion of the catheter shaft in a first curve direction.

In Example 9, further to the apparatus of Example 8, the actuator is configured to reduce the tension on the first line in response to movement of the actuator in a proximal direction relative to the housing from a distal position.

In Example 10, further to the apparatus of Example 9, the actuator is configured to curve the distal portion of the catheter shaft to a neutral position in response to movement of the actuator in the proximal direction relative to the housing from the distal position.

In Example 11, further to the apparatus of any one of Examples 6-10, the actuator includes a neutral position relative to the housing and the first line and the second line lack tension in response to the actuator being in the neutral position.

In Example 12, further to the apparatus of Example 11, the actuator is configured to create tension on second line to engage the second anchor with the second pocket in response to movement of the actuator in a proximal direction relative to the neutral position.

In Example 13, further to the apparatus of Example 12, the actuator is configured to apply the tension on the second line to curve the distal portion of the catheter shaft in a second curve direction that is opposite to the first curve direction of the distal portion of the catheter shaft.

In Example 14, further to the apparatus of any one of Examples 1-10, the actuator and the piston assembly are configured to maintain a position of the distal portion of the catheter shaft in the absence of force applied by the user.

In Example 15, further to the apparatus of Example 14, the apparatus further includes an o-ring configured to apply a hold force between the actuator and the piston assembly.

In Example 16, a steerable catheter handle apparatus includes a housing; a catheter shaft including a proximal portion, a distal portion, and an intermediate portion extending between the proximal portion and the distal portion; an actuator coupled to the catheter shaft and configured to move longitudinally relative to the housing and longitudinally move the catheter shaft in response to force imparted by a user; a piston assembly arranged within the housing and configured to receive the actuator and allow longitudinal movement of the actuator relative to the housing; and two steering lines each including a distal end attached to the distal portion of the catheter shaft and a proximal portion configured to engage an end cap of the piston assembly in response to the longitudinal movement of the actuator and alter tension on the steering lines to effect curvature of the distal portion of the catheter shaft.

In Example 17, further to the apparatus of Example 16, the steerable catheter handle apparatus also includes a pulley assembly arranged within the housing and configured to translate in a direction common with the actuator in response to force imparted by the user on the actuator.

In Example 18, further to the apparatus of Example 17, the pulley assembly is coupled to the piston assembly by one or more supports.

In Example 19, further to the apparatus of Example 18, at least one of the two steering lines are arranged about the pulley assembly.

In Example 20, further to the apparatus of Example 19, the two steering lines include a first line and a second line, and further comprising a first anchor attached to the proximal portion of the first line, and a second anchor attached to the proximal end of the second line.

In Example 21, further to the apparatus of Example 20, the first anchor is configured to engage the end cap of the piston assembly in response to the movement of the actuator.

In Example 22, further to the apparatus of Example 21, the actuator is configured to create tension on the first line to engage the first anchor with the end cap in response to movement of the actuator in a distal direction relative to the housing and to curve the distal portion of the catheter shaft in a first curve direction.

In Example 23, further to the apparatus of Example 22, the actuator is configured to reduce the tension on the first line in response to movement of the actuator in a proximal direction relative to the housing from a distal position.

In Example 24, further to the apparatus of Example 23, the actuator is configured to curve the distal portion of the catheter shaft to a neutral position in response to movement of the actuator in the proximal direction relative to the housing from the distal position.

In Example 25, a steerable catheter handle apparatus includes a housing; a catheter shaft includes a proximal portion, a distal portion, and an intermediate portion extending between the proximal portion and the distal portion; an actuator coupled to the catheter shaft and configured to move longitudinally relative to the housing and longitudinally move the catheter shaft in response to force imparted by a user; a piston assembly arranged within the housing and configured to receive the actuator and allow longitudinal movement of the actuator relative to the housing; a pulley assembly arranged distal to the piston assembly; and two steering lines arranged about the pulley assembly and each including a distal end attached to the distal portion of the catheter shaft an anchor at a proximal portion configured to engage the piston assembly in response to the longitudinal movement of the actuator and alter tension on the steering lines to effect curvature of the distal portion of the catheter shaft in a first direction.

In Example 26, further to the apparatus of Example 25, the actuator is configured to alter an amount of steering on the distal portion of the catheter shaft in response to movement between a neutral position relative to the housing and a distal position relative to the housing.

In Example 27, further to the apparatus of Example 26, the actuator is configured to create tension on the one of the two steering lines to engage the anchor with the piston assembly in response to movement of the actuator toward the distal position to curve the distal portion of the catheter shaft in a first curve direction.

In Example 28, further to the apparatus of Example 27, the actuator is configured to curve the distal portion of the catheter shaft to a neutral position in response to movement of the actuator in the toward the neutral position from the distal position.

In Example 29, further to the apparatus of Example 28, the actuator further includes a proximal position relative to the housing and the actuator is configured to curve the distal portion of the catheter shaft in a second curve direction that is opposite to the first curve direction of the distal portion of the catheter shaft in response to movement of the actuator toward the proximal position from the neutral position.

In Example 30, further to the apparatus of Example 29, the actuator is configured to curve the distal portion of the catheter shaft to the neutral position in response to movement of the actuator in the toward the neutral position from the proximal position In Example 31, further to the apparatus of Example 26, the actuator and the piston assembly are configured to maintain a position of the distal portion of the catheter shaft in the absence of force applied by the user.

In Example 32, further to the apparatus of Example 31, the apparatus also includes an o-ring configured to apply a hold force between the actuator and the piston assembly.

In Example 33, a method for steering of a catheter shaft includes arranging the catheter shaft, having a proximal portion, a distal portion, and an intermediate portion extending between the proximal portion and the distal portion, of a catheter handle at a target location within a patient, the catheter handle including a housing, an actuator coupled to the catheter shaft, a piston assembly arranged within the housing and configured to receive the actuator and allow longitudinal movement of the actuator relative to the housing, a pulley assembly arranged distal to the piston assembly, and a first steering and a second steering line arranged about the pulley assembly and each including a distal end attached to the distal portion of the catheter shaft and an anchor at a proximal portion; moving the actuator in a distal direction relative to the housing, such that a first anchor at the proximal end of a first line attached to the catheter shaft engages a first pocket, creating tension on the first line; moving the actuator in a proximal direction relative to the housing, such that the first anchor shifts away from the first pocket, releasing tension on the first line; and moving the actuator in a proximal direction further relative to the housing, such that a second anchor at the proximal end of a second line attached to the catheter shaft engages a second pocket, create tension on the second line.

In Example 34, further to the method of Example 33, the tension on the first line curves the distal portion of the catheter shaft in a first direction, and the tension on the second line curves the distal portion of the catheter shaft in the opposite direction to the first direction.

In Example 35, further to the method of Example 34, the pulley assembly is configured to move in a direction common with the actuator in response to movement of the actuator.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 3 shows another interior view of a portion of an example catheter handle, in accordance with various aspects of the present disclosure.

FIG. 4A shows a partial interior view of an example catheter handle with an actuator in a neutral position, in accordance with various aspects of the present disclosure.

FIG. 4B shows a close-up view of a portion of the catheter handle shown in FIG. 4A.

FIG. 4C shows a partial interior view of the catheter handle, shown in FIGS. 4A-B, with the actuator in a distal position, in accordance with various aspects of the present disclosure.

FIG. 4D shows a close-up view of a portion of the catheter handle shown in FIG. 4C.

FIG. 4E shows a partial interior view of the catheter handle, shown in FIGS. 4A-D, with the actuator in a proximal position, in accordance with various aspects of the present disclosure.

FIG. 4F shows a close-up view of a portion of the catheter handle shown in FIG. 4E.

Figure 1:
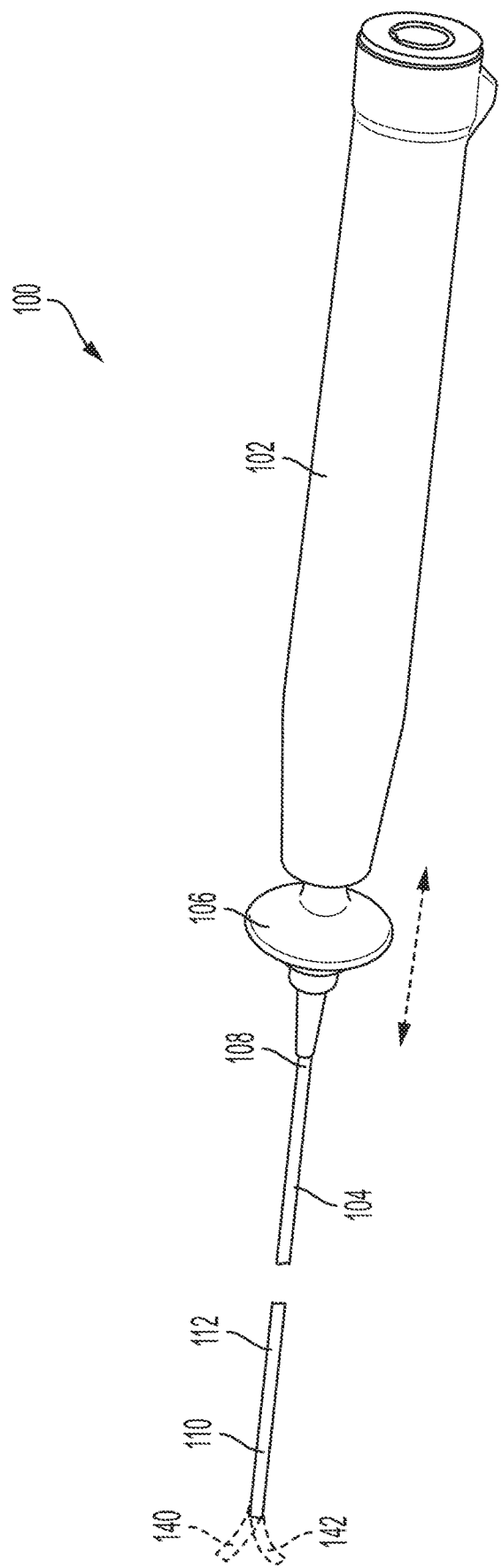
FIG. 1 shows an illustration of an example catheter handle, in accordance with various aspects of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various aspects of the present disclosure are directed toward apparatuses, systems, and methods that include a catheter body that is steerable, deflectable, or curveable. The catheter handles, as discussed in further detail below, may be configured to curve or steer a distal end portion of a catheter shaft, extending from the catheter handle, in one or more directions. In certain instances, the catheter handles may include an actuator that, when moved by a user relative to the catheter handle, steers or curves the distal portion of the catheter shaft. The distal end portion may include therapeutic elements (e.g., electrode structures to deliver ablation energy) Curving of the distal end portion of the catheter may enable delivery of therapeutic energy to a target tissue area within a patient.

FIG. 1 shows an illustration of an example catheter handle 100, which includes a housing 102, a catheter shaft 104, and an actuator 106, in accordance with various aspects of the present disclosure. The catheter shaft 104 includes a proximal portion 108, a distal portion 110, and an intermediate portion 112 extending between the proximal portion 108 and the distal portion 110.

The actuator 106 is coupled to the catheter shaft 104 and configured to move longitudinally relative to the housing 102 in response to force imparted by a user. Movement of the actuator 106 relative to the housing 102 curves the distal portion 110 of the catheter shaft 104 in one or both of a first curve direction 140 and a second curve direction 142. In certain instances, the handle 100 may be configured to curve the distal portion 110 of the catheter shaft 104 in only one of the first curve direction 140 or the second curve direction 142.

As shown, the actuator 106 is in a neutral position. When the actuator 106 is in the neutral position (e.g., a pre-set distance relative to the housing 102), the distal portion 110 of the catheter shaft 104 is uncurved or unbiased. The actuator 106 being moved distal relative to the housing 102 effects curvature of the distal portion 110 of the catheter shaft 104 in one of the first curve direction 140 or the second curve direction 142. Movement of the actuator 106 proximally, after moving the actuator 106 distally, back toward the neutral position effects curvature of the distal portion 110 of the catheter shaft 104 from one of the first curve direction 140 or the second curve direction 142 to the uncurved or unbiased arrangement.

In certain instances, the actuator 106 may not be moved proximally relative to the housing 102 relative to the neutral position. In other instances, the actuator 106 may be moved proximally relative to the housing 102 from the neutral position without curving of the distal portion 110 of the catheter shaft 104. In each of these instances, the catheter handle 100 is unidirectional and effects curvature of the distal portion 110 of the catheter shaft 104 in only one of the first curve direction 140 and the second curve direction 142.

In other instances, the actuator 106 may be moved proximally relative to the housing 102 from the neutral position to effect curvature of the distal portion 110 of the catheter shaft 104 in one of the first curve direction 140 or the second curve direction 142. In these instances, moving the actuator 106 distally relative to the neutral position effects curvature of the distal portion 110 of the catheter shaft 104 in one of the first curve direction 140 and the second curve direction 142, and moving the actuator 106 proximally relative to the neutral position effect curvature of the distal portion 110 of the catheter shaft 104 in the other of the first curve direction 140 or the second curve direction 142. Movement of the actuator toward the neutral position relative to the proximal or distal position effects curvature of the distal portion 110 of the catheter shaft 104 to the uncurved or unbiased arrangement.

Steering lines (not shown) are arranged within the catheter shaft 104 and attached or coupled to portions of the distal portion 110. As described in further details below, the interactions of the actuator 106 with various internal components, including steering lines, of the housing 102 effectuates the one or more curve directions 140, 142 as described in further detail below.

Figure 2:
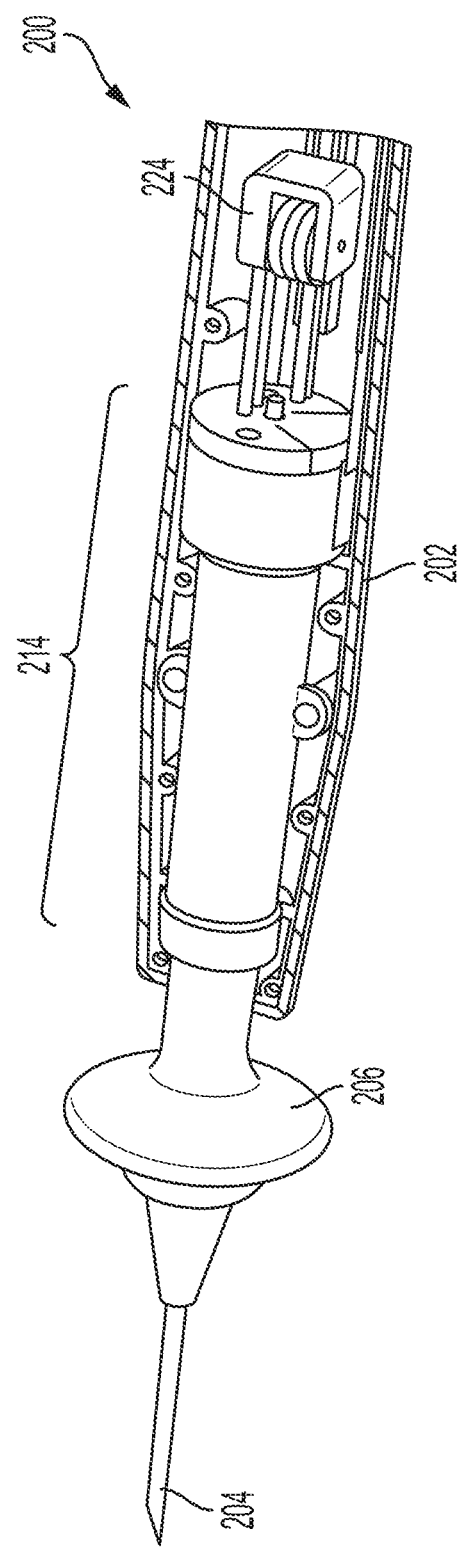
FIG. 2 shows an interior view of a portion of an example catheter handle, in accordance with various aspects of the present disclosure.

FIG. 2 shows an interior view of a portion of an example catheter handle 200, in accordance with various aspects of the present disclosure. The catheter handle 200 includes a housing 202, a catheter shaft 204, and an actuator 106. The piston assembly 214 is arranged within the housing 202 and configured to receive the actuator 206 and allow longitudinal movement of the actuator 206 relative to the housing 202. As noted above with reference to FIG. 1, the piston assembly 214 may be moved at least one of proximally and distally relative to the housing 202. In addition, the catheter shaft 204 may be attached, adhered, or couple to the actuator 206. Thus, when a user moves the actuator 206, the catheter shaft 204 also moves along with the actuator 206.

In certain instances, the catheter handle 200 also includes a pulley assembly 224 arranged within the housing 202. The pulley assembly 224 may interact with one or more steering lines (not shown) that are arranged through an interior of the piston assembly 214, an interior of the actuator 206, and through an interior of the catheter shaft 204. As noted above with reference to FIG. 1, the one or more steering lines are anchored or attached to the interior of the catheter shaft 204 at or near a distal end thereof. In addition, one or more steering lines are arranged about the pulley assembly 224. As described in further detail with reference to FIG. 3 and FIGS. 4A-F, a distal end portion, adjacent or near where the one or more steering lines are anchored or attached, may curve in one or more directions by way of movement of the actuator 206 by way of the catheter shaft 204 being attached to the actuator 206 and tension on the one or more steering lines.

FIG. 3 shows another interior view of a portion of an example catheter handle 300, in accordance with various aspects of the present disclosure. The catheter handle 300 includes a housing 302, a catheter shaft (not shown), and an actuator 306. The catheter handle 300 includes one or more lines 326, 328. The one or more lines 326, 328 includes a distal end attached to the distal portion of the catheter shaft 110 (as described in distal above) and a proximal end configured to engage an end cap 322 of the piston assembly 314 in response to the longitudinal movement of the actuator 306 to effect curvature of the distal portion 110 of the catheter shaft 104 (as shown in FIG. 1).

In some instances, at least one of the two lines 326, 328 are arranged about the pulley assembly 324. In other instances, both lines 326, 328 are arranged about the pulley assembly 324. In some instances, the one or more lines 326, 328 include a first line 326 and a second line 328. In other instances, the one or more lines 326, 328 could be one continuous line. The one or more lines 326, 328 may further include a first anchor 330 attached to the proximal end of the first line 326, and a second anchor 332 attached to the proximal end of the second line 328.

The first anchor 330 may be configured to engage the end cap 322 of the piston assembly 314 in response to the movement of the actuator 306. In some instances, the end cap 322 of the piston assembly 314 includes a first pocket 334 and a second pocket 336, and the first anchor 330 is configured to engage the first pocket 334 of the piston assembly 314, and the second anchor 332 is configured to engage the second pocket 336 of the piston assembly 314 in response to movement of the actuator 306. As described in further detail below with reference to FIGS. 4A-F, tension on the lines 326, 328 by way of movement of the actuator 306 within the piston assembly 314 effects curvature of a distal end portion of the catheter shaft.

FIG. 4A shows a partial interior view of an example catheter handle 400 with the actuator 406 in a neutral position, in accordance with various aspects of the present disclosure. The catheter handle 400 includes a housing 402, a catheter shaft 404, and an actuator 406, and a piston assembly 414. A proximal portion 408 of the catheter shaft 404 may be coupled to the actuator 406, so that the catheter shaft 404 moves along with the actuator 406 in response to force imparted by a user. In some instances, when the actuator 406 is in the neutral position relative to the housing 402, a first line 426 and a second line 428 lack tension in response to the actuator 406 being in the neutral position, and a distal portion 410 of the catheter shaft 410 is not curved, as will be discussed in more details below in FIG. 4B.

In some instances, a pulley assembly 324 is arranged within the housing 302. The first line 426 and the second line 428 interact with and may be arranged about the pulley assembly 424. The pulley assembly 424 may be attached or coupled to the actuator 406 by way of supports 438.

FIG. 4B shows a close-up view of a portion of the catheter handle 400 shown in FIG. 4A. As shown, the piston assembly 414 includes an end cap 422. The lines 426, 428 may be configured to engage the end cap 422 of the piston assembly 414 in response to the longitudinal movement of the actuator 406 to effect curvature of the distal portion 410 of the catheter shaft 104 (as shown in FIG. 1). The end cap 422 includes pockets 434, 436 that may interact with anchors 430, 432 attached or couple to the lines 426, 428. The pockets 434, 436 may be arranged on opposing sides of the end cap 422 as shown in FIG. 4B. In certain instances, the lines 426, 428 are arranged about the pulley assembly 424 such that the respective anchors 430, 432 engage the pockets 434, 436 in response to movement of the actuator 406 as described in further detail below.

When the actuator 406 is in the neutral position, the anchors 430, 432 may not be engaged with the pockets 434, 436. In these instances, the tension is lacking on the lines 426, 428. Without tension on the lines 426, 428, the distal portion 410 of the catheter shaft 404 is uncurved or unbiased. As described in further detail below, tension may created by way of the lines 426, 428 being attached to an interior of the distal portion 410 of the catheter shaft 404 and one or more of the anchors 430, 432 engaging with the pockets 434, 436. Tension on the lines 426, 428 may effect curvature due to the points of the lines 426, 428 due to movement of the catheter shaft 404 during movement of the actuator 406.

A distance between the end cap 422 of the piston assembly 414 and the pulley assembly 424 may be arranged such that neither of the anchors 430, 432 is engaged into their respective pockets 434, 436 when the actuator 406 is in the neutral position. In some instances, the distance between the end cap 422 of the piston assembly 414 and the pulley assembly 424 is related to the amount of travel forward and backward of the actuator 406. In certain instances, a position of the pulley assembly 424 may be adjusted distally and proximally along the supports 438 to enable more or less curvature in one or both steering directions. In addition, the position of the pulley assembly 424 may be adjusted to provide additional distal travel for additional articulation/curvature. The distance of the pulley assembly 424 adjustability may allow for customization of the curvature and articulation.

FIG. 4C shows a partial interior view of the catheter handle 400 with the actuator 406 in a distal position relative to the neutral position shown in FIG. 4A and FIG. 4B. The distance between the actuator 406 and the housing 402 is greater as compared to the neutral position. In certain instances, the pulley assembly 424 also may move distally with the piston assembly 406 due to the coupling therebetween by way of the one or more supports 438.

In some instances, when the actuator 406 is moving in a distal direction relative to the housing 402, the distance between the actuator 406 and the piston assembly 414 becomes greater, whereas the distance between the pulley assembly 424 and the piston assembly 414 becomes shorter. In some instances, when the actuator 406 is in the distal position relative to the housing 402, tension is created on the first line 426, whereas the second line 428 lacks tension, and the distal portion 410 of the catheter shaft 404 is curved in the first curve direction 440, as will be discussed in more details below in FIG. 4D. As the actuator 406 is moved distally, the amount of curvature increases.

FIG. 4D shows a close-up view of a portion of the catheter handle 400 shown in FIG. 4C. When the actuator 406 moves in the distal direction relative to the housing 402, the pulley assembly 424, when coupled to the actuator 406, moves along with the actuator 406 in the distal direction relative to the housing 402. As the distance between the pulley assembly 424 and the piston assembly 414 becomes shorter, the first anchor 430 engages with the first pocket 434, creating tension in the first line 426. The tension in the first line 426 may curve the distal portion 410 of the catheter shaft 404 in a first curve direction 440 (as shown in FIG. 4C).

In some instances, when the actuator 406 moves in the distal direction relative to the housing 402, the second anchor 432 moves in the distal direction relative to the housing 402 and away from the second pocket 436, and no tension is created on the second line 428. In other instances, the actuator 406 and the piston assembly 414 are configured to maintain a position of the distal portion of the catheter shaft 410 in the absence of force applied by the user.

In some instances, the actuator 406 is configured to alter an amount of steering on the distal portion of the catheter shaft 410 in response to relative movement between the neutral position relative to the housing 402 and the distal position relative to the housing 402. The greater the distance the actuator 406 is moved from the housing 402, the greater the amount of curvature on the distal end 410 of the catheter shaft 404. Tension is maintained on the first line 426 in the absence of force applied by the user on the actuator 406. As a result, the amount of curvature on the distal end 410 of the catheter shaft 404 is maintained in the absence of the force applied by the user. In addition, the actuator 406 is configured to curve the distal portion 410 of the catheter shaft 404 towards the neutral position in response to movement of the actuator 406 to the neutral position from the distal position. Tension is relieved on the first line 426 as the actuator 406 is moved proximally from the distal position and the amount of curvature on the distal end 410 of the catheter shaft 404 is reduced.

FIG. 4E shows a partial interior view of an example catheter handle with the actuator 406 in a proximal position relative to the neutral position shown in FIG. 4A and FIG. 4B. In some instances, when the actuator 406 is moving in a proximal direction relative to the housing 402, the distance between the actuator 406 and the piston assembly 414 becomes shorter. In instances where actuator 406 is coupled to the pulley assembly 424, the distance between the pulley assembly 424 and the piston assembly 414 becomes longer as the pulley assembly 424 moves in the proximal direction relative to the housing 402. In some instances, when the actuator 406 is in the proximal position relative to the housing 402, tension is created on the second line 428, and the distal portion of the catheter shaft 410 is curved in the second curve direction 442, as will be discussed in more details below in FIG. 4F. In some instances, the first curve direction 440 is opposite to the second curve direction 442.

FIG. 4F shows a close-up view of a portion of the catheter handle 400 shown in FIG. 4E. When the actuator 406 moves in the proximal direction relative to the housing 402, the pulley assembly 424, when coupled to the actuator 406, moves along with the actuator 406 in the proximal direction relative to the housing 402. As the distance between the pulley assembly 424 and the piston assembly 414 becomes longer, the second anchor 432 engages with the second pocket 436, creating tension in the second line 428. The tension in the second line 428 may curve the distal portion of the catheter shaft 410 in the second curve direction 442. The greater the distance the actuator 406 is moved from the housing 402, the greater the amount of curvature on the distal end 410 of the catheter shaft 404. Tension is maintained on the second line 426 in the absence of force applied by the user on the actuator 406 until the actuator 406 has been moved. As a result, the amount of curvature on the distal end 410 of the catheter shaft 404 is maintained in the absence of the force applied by the user (e.g., as a result of the o-ring described with reference to FIG. 5).

In some instances, when the actuator 406 moves in the proximal direction relative to the housing 402, the first anchor 430 moves in the proximal direction relative to the housing 402 and away from the first pocket 434, and no tension is created on the first line 426. As noted above, the actuator 406 and the piston assembly 414 are configured to maintain a position of the distal portion of the catheter shaft 410 in the absence of force applied by the user. Tension is relieved on the second line 428 as the actuator 406 is moved distally from the proximal position and the amount of curvature on the distal end 410 of the catheter shaft 404 is reduced.

In certain instances, the catheter handle 400 may be configured for unidirectional steering rather than bidirectional steering. In these instances, the actuator 406 may be configured to move only distally or only proximally relative to a neutral position to curved the distal portion 410 of the catheter shaft 404 in one direction. One of the lines 426, 428 may also lack and one of the anchors 430, 432 such that tension may not be created when the actuator 406 is moved in one of the directions detailed above.

Figure 5:
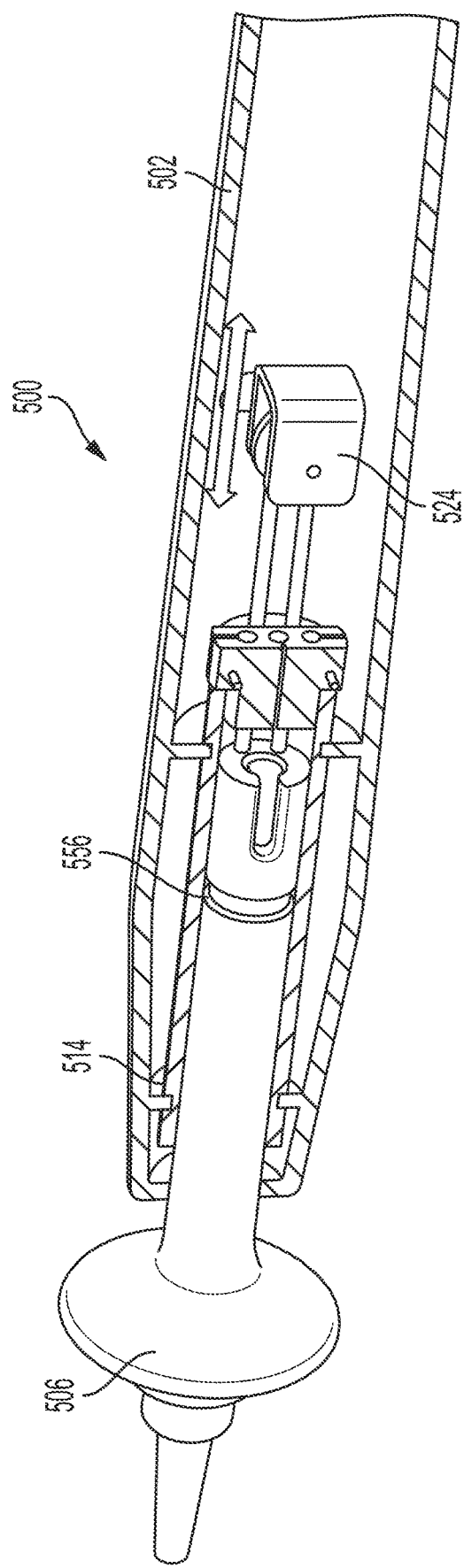
FIG. 5 shows a partial interior view of an example catheter handle with a hold-force o-ring, in accordance with various aspects of the present disclosure.

FIG. 5 shows a partial interior view of an example catheter handle 500 with a hold-force o-ring, in accordance with various aspects of the present disclosure. The catheter handle 500 includes a housing 502, a catheter shaft (not shown), an actuator 506, a piston assembly 514, and a pulley assembly 524, as described in detail above. The o-ring 556 may be configured to apply a hold force between the actuator 506 and the piston assembly 514.

In certain instances, the o-ring 556 is arranged with the actuator 506 within the piston assembly 514. The o-ring 556 may provide a hold-force such that the force is required to move the actuator 506 within the piston assembly 514. A size of the o-ring 556 may be adjusted to alter an amount of force required to overcome friction between the actuator 506 within the piston assembly 514. In certain instances, the length between the pulley assembly 524 and the piston assembly 514 may be adjusted to relate to an amount of tension on lines. A greater length between the pulley assembly 524 and the piston assembly 514 may also adjust the force required to move the actuator 506 due to greater tension on the lines.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A steerable catheter handle apparatus, the apparatus comprising:
   a housing;
   a catheter shaft including a proximal portion, a distal portion, and an intermediate portion extending between the proximal portion and the distal portion;
   an actuator coupled to the catheter shaft and configured to move longitudinally relative to the housing and longitudinally move the catheter shaft in response to force imparted by a user;
   a pulley assembly arranged within the housing and configured to translate in a direction common with the actuator in response to force imparted by the user on the actuator;
   a piston assembly arranged within the housing and configured to receive the actuator and allow longitudinal movement of the actuator relative to the housing; and
   two steering lines each including a distal end attached to the distal portion of the catheter shaft and a proximal portion configured to engage an end cap of the piston assembly in response to the longitudinal movement of the actuator and alter tension on the steering lines to effect curvature of the distal portion of the catheter shaft.

2. The apparatus of claim 1, wherein the pulley assembly is coupled to the piston assembly by one or more supports.

3. The apparatus of claim 2, wherein at least one of the two steering lines are arranged about the pulley assembly.

4. The apparatus of claim 3, wherein the two steering lines include a first line and a second line, and further comprising a first anchor attached to the proximal portion of the first line, and a second anchor attached to the proximal end of the second line.

5. The apparatus of claim 4, wherein the first anchor is configured to engage the end cap of the piston assembly in response to the movement of the actuator.

6. The apparatus of claim 5, wherein the actuator is configured to create tension on the first line to engage the first anchor with the end cap in response to movement of the actuator in a distal direction relative to the housing and to curve the distal portion of the catheter shaft in a first curve direction.

7. The apparatus of claim 6, wherein the actuator is configured to reduce the tension on the first line in response to movement of the actuator in a proximal direction relative to the housing from a distal position.

8. The apparatus of claim 7, wherein the actuator is configured to curve the distal portion of the catheter shaft to a neutral position in response to movement of the actuator in the proximal direction relative to the housing from the distal position.

9. A steerable catheter handle apparatus, the apparatus comprising:
a housing;
a catheter shaft including a proximal portion, a distal portion, and an intermediate portion extending between the proximal portion and the distal portion;
an actuator coupled to the catheter shaft and configured to move longitudinally relative to the housing and longitudinally move the catheter shaft in response to force imparted by a user;
a piston assembly arranged within the housing and configured to receive the actuator and allow longitudinal movement of the actuator relative to the housing; and
a first steering line and a second steering line each including a distal end attached to the distal portion of the catheter shaft and a proximal portion configured to engage an end cap of the piston assembly in response to the longitudinal movement of the actuator and alter tension on the steering lines to effect curvature of the distal portion of the catheter shaft;
wherein each proximal portion includes an anchor attached to the proximal portion and configured to engage the end cap of the piston assembly in response to the movement of the actuator.

10. The apparatus of claim 9, wherein the actuator is configured to create tension on the first line to engage the anchor with the end cap in response to movement of the actuator in a distal direction relative to the housing and to curve the distal portion of the catheter shaft in a first curve direction.

11. The apparatus of claim 10, wherein the actuator is configured to reduce the tension on the first line in response to movement of the actuator in a proximal direction relative to the housing from a distal position.

12. The apparatus of claim 11, wherein the actuator is configured to curve the distal portion of the catheter shaft to a neutral position in response to movement of the actuator in the proximal direction relative to the housing from the distal position.

* * * * *